(12) United States Patent
    Shankarsetty

(10) Patent No.: US 10,792,472 B2
(45) Date of Patent: Oct. 6, 2020

(54) APPARATUS AND ASSOCIATED METHODOLOGIES FOR CREATING A STOMA

(71) Applicant: Covidien LP, Mansfield, MA (US)

(72) Inventor: Jeevan Maddur Shankarsetty, Karnataka (IN)

(73) Assignee: Covidien LP, Mansfield, MA (US)

( * ) Notice: Subject to any disclaimer, the term of this patent is extended or adjusted under 35 U.S.C. 154(b) by 264 days.

(21) Appl. No.: 15/873,060

(22) Filed: Jan. 17, 2018

(65) Prior Publication Data

US 2018/0236207 A1    Aug. 23, 2018

Related U.S. Application Data

(60) Provisional application No. 62/462,039, filed on Feb. 22, 2017.

(51) Int. Cl.
    *A61M 25/06* (2006.01)
    *A61F 5/445* (2006.01)
    (Continued)

(52) U.S. Cl.
    CPC ..... *A61M 25/0662* (2013.01); *A61B 17/1114* (2013.01); *A61F 5/445* (2013.01); *A61B 17/0682* (2013.01); *A61B 17/1155* (2013.01); *A61B 17/3462* (2013.01); *A61B 2017/1121* (2013.01); *A61B 2017/1135* (2013.01); *A61F 5/443* (2013.01); *A61F 5/4407* (2013.01)

(58) Field of Classification Search
    CPC ............ A61B 17/0682; A61B 17/1114; A61B 17/1115; A61B 17/3462; A61B 2017/1121; A61B 2017/1125; A61M 25/0662; A61F 5/445
    See application file for complete search history.

(56) References Cited

U.S. PATENT DOCUMENTS 5,443,197 A    8/1995  Malis et al.
5,662,664 A *  9/1997  Gordon .............. A61B 17/0469
                                                      112/169
(Continued)

FOREIGN PATENT DOCUMENTS

KR    20110129154 A    12/2011

OTHER PUBLICATIONS

European Search Report dated Jul. 12, 2018, corresponding to European Application No. 18157818.8; 8 pages.

*Primary Examiner* — Tuan V Nguyen
(74) *Attorney, Agent, or Firm* — Carter, DeLuca & Farrell LLP

(57) ABSTRACT

A surgical apparatus used in an ostomy procedure includes an introducer configured for atraumatic insertion in a tissue opening and a dilator. The dilator includes an elongate body and an extension movably coupled to the elongate body. A distal portion of the elongate body is disposed within and axially movable relative to the introducer between first and second positions. The extension is configured to move from a retracted state to an expanded state in response to movement of the dilator relative to the introducer from the first position to the second position. In the retracted state, the extension is disposed within the introducer, and in the expanded state the extension projects laterally outward from the distal portion of the elongate body.

19 Claims, 9 Drawing Sheets

(51) Int. Cl.
*A61B 17/11* (2006.01)
*A61B 17/34* (2006.01)
*A61F 5/44* (2006.01)
*A61F 5/443* (2006.01)
*A61B 17/115* (2006.01)
*A61B 17/068* (2006.01)

(56) References Cited

U.S. PATENT DOCUMENTS

| | | | |
|---|---|---|---|
| 2002/0045908 A1* | 4/2002 | Nobles | A61B 17/0057 606/144 |
| 2003/0028201 A1 | 2/2003 | Navarro et al. | |
| 2003/0167063 A1* | 9/2003 | Kerr | A61B 17/0057 606/144 |
| 2011/0190793 A1* | 8/2011 | Nobles | A61B 17/0469 606/144 |
| 2015/0115015 A1 | 4/2015 | Prescott et al. | |

* cited by examiner

APPARATUS AND ASSOCIATED METHODOLOGIES FOR CREATING A STOMA

CROSS-REFERENCE TO RELATED APPLICATIONS

This application claims the benefit of and priority to U.S. Provisional Patent Application Ser. No. 62/462,039, filed Feb. 22, 2017, the entire disclosure of which is incorporated by reference herein.

TECHNICAL FIELD

The present disclosure generally relates to a surgical apparatus and associated methods for establishing a stoma, and, in particular, an apparatus for assisting in securing the end margins of an intestine about an opening in an abdominal wall in an ostomy procedure.

BACKGROUND

Exteriorization of an internal body vessel such as the intestine is called a stoma. Stomas may be created in conjunction with an ostomy procedure by securing a bisected portion of an intestine to the abdominal wall to provide internal access into the intestine for collecting fecal matter.

Ostomy surgery is sometimes performed on an emergency basis due to diverticulitis, trauma, radiation complications, volvulus, necrotic bowel, bowel perforation, etc. Children and adults alike may require an ostomy. An ostomy may only be temporary to allow for healing of the bowel or a decrease of inflammation at the surgical site. In some instances an ostomy may be permanent.

The most typical ostomy surgery is the Standard or Brooke ileostomy, in which an end of the ileum (i.e., small intestine) is pulled through the abdominal wall and is turned back and sutured to the skin, leaving a smooth, rounded, inside-out ileum as the stoma. The stoma is often formed in the right lower part of the abdomen and on a flat surface of healthy and smooth skin. In the Standard or Brooke ileostomy, fecal output is not controlled, and thus requires the patient to wear a collection pouch which receives fecal output from the stoma.

Another ostomy procedure is a loop colostomy. A loop colostomy involves pulling a loop of colon through an incision in the abdomen. The colon is then flared outwardly and fastened (e.g., stitched) to the skin of the patient to form a stoma. In this procedure, the stoma includes two openings immediately adjacent one another, wherein one of the openings is connected to the functioning part of the patient's bowel and is used to discharge waste products, and the other of the two openings is connected to the inactive part of the patient's bowel leading to the rectum.

A third ostomy procedure is an end colostomy, in which an end of a patient's colon is pulled out through an incision in the patient's abdomen and fastened (e.g., stitched) to the skin of the patient to form a stoma.

In all of the ostomy procedures described above, intestinal tissue, whether it be from the small intestine or the large intestine, is secured to the abdominal wall and/or cutaneous tissue of the abdomen. Securing the intestinal tissue to the abdominal wall and/or cutaneous tissue of the abdomen keeps the stoma in the desired location and prevents it from withdrawing back into the abdominal cavity. A need exists to develop apparatuses and methods for assisting in securing a bisected portion of the intestine to the abdominal wall and/or the cutaneous tissue of the abdomen during an ostomy procedure in which a stoma is to be formed.

SUMMARY

In one aspect of the present disclosure, provided is a surgical apparatus used in an ostomy procedure. The surgical apparatus includes an introducer configured for atraumatic insertion into a tissue opening and a dilator. The dilator includes an elongate body and an extension movably coupled to the elongate body. The elongate body has a distal portion disposed within the introducer. The elongate body is axially movable relative to the introducer from a first position to a second position. The extension is movable from a retracted state to an expanded state in response to movement of the dilator relative to the introducer from the first position to the second position. In the retracted state the extension is disposed within the introducer, and in the expanded state the extension projects laterally outward from the distal portion of the elongate body.

In some embodiments, the dilator may be configured to move axially relative to the introducer between the first position and the second axial position, in which the extension of the dilator is disposed outside of the introducer.

In some embodiments, the dilator may slide proximally relative to the introducer from the first position to the second position.

In some embodiments, the introducer may be configured to prevent the dilator from moving proximally relative to the introducer when the dilator is in the second position.

In some embodiments, the dilator may have a mating surface disposed at the distal portion of the elongate body and the introducer may have a mating surface disposed at a proximal portion thereof such that the mating surface of the dilator contacts the mating surface of the introducer in the second position.

In some embodiments, the dilator may include a biasing member disposed within the elongate body. The biasing member may be configured to bias the extension toward the expanded state.

In some embodiments, the extension may have a proximal end portion pivotably coupled to the elongate body and disposed within the elongate body. The biasing member may be in engagement with the proximal end portion of the extension.

In some embodiments, the extension may have a proximal end portion pivotably coupled to the elongate body and a distal end portion. The distal end portion may rotate in a proximal direction during movement of the extension from the retracted state to the expanded state. The distal portion of the elongate body may have a stop configured to engage the distal end portion of the extension when the extension is moved to the expanded state.

In some embodiments, the distal end portion of the extension may be disposed in oblique relation to the proximal end portion thereof.

In some embodiments, in the expanded state, the proximal end portion of the extension may be substantially perpendicular with a longitudinal axis defined by the elongate body and the distal end portion may be angled in a distal direction relative to the longitudinal axis.

In some embodiments, the distal end portion of the extension may be in engagement with an inner wall of the introducer when the extension is in the retracted state. The dilator may be movable in a proximal direction relative to the introducer between the first position, in which the distal end portion of the extension is in engagement with the inner wall of the introducer, and the second position, in which the distal end portion of the extension is out of engagement with the inner wall of the introducer.

In some embodiments, the extension may include a plurality of extensions disposed circumferentially about the distal portion of the elongate body.

In another aspect of the present disclosure, methods of performing an ostomy procedure are presented. The methods may include inserting an introducer into a tissue opening while maintaining a dilator disposed within the introducer in a retracted state. An elongate body of the dilator is then moved proximally relative to the introducer to transition the dilator from the retracted state, in which an extension movably coupled to the elongate body is disposed within a cavity of the introducer, to an expanded state, in which the extension projects laterally outward from the elongate body into engagement with a piece of tissue adjacent the tissue opening.

Some methods may further include moving the elongate body of the dilator distally relative to the tissue opening after the dilator is in the expanded state, thereby urging, with the extension, the piece of tissue into engagement with a portion of tissue that surrounds the opening. The methods may further include fastening the piece of tissue to the portion of tissue surrounding the tissue opening to form an ostomy.

In some methods, the extension may pivot relative to the elongate body as the elongate body moves proximally relative to the introducer. The extension may begin to pivot relative to the elongate body upon the extension moving out of engagement with an inner wall of the introducer.

In some methods, the extension may be a plurality of extensions disposed circumferentially about a distal portion of the elongate body such that each of the plurality of extensions is engaged to a different sector of the piece of tissue when the dilator is in the expanded state.

Other features of the present disclosure will be appreciated from the following description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Particular embodiments of the present disclosure are described hereinbelow with reference to the accompanying drawings. However, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

As used herein, the term distal refers to that portion of the surgical apparatus, which is farthest from a clinician, while the term proximal refers to that portion of the surgical apparatus, which is closest to the clinician. In addition, as used herein, the term clinician refers to medical staff including doctors, nurses and support personnel.

The following description of the surgical apparatus will focus on its application in facilitating the formation of a stoma in an ostomy procedure, particularly, maintaining patency of an intestine as end margins thereof are being fastened to abdominal tissue in connection with a colostomy or ileostomy procedure. However, the surgical apparatus has application in other ostomy procedures including urostomy, gastrostomy, and jejunostomy procedures.

Figure 1:
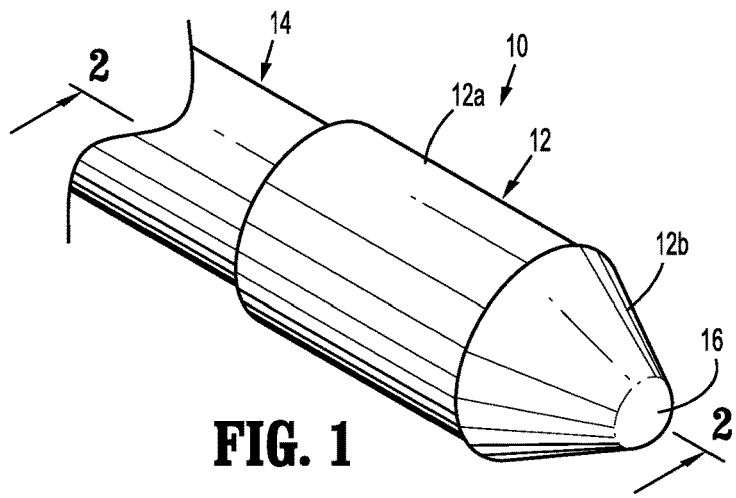
FIG. 1 is a perspective view of an embodiment of a surgical apparatus for facilitating formation of a stoma within abdominal tissue illustrating an introducer and a dilator thereof.

FIG. 1 illustrates an embodiment of a surgical apparatus for use in an ostomy procedure, and is identified generally using reference numeral 10. The surgical apparatus 10 generally includes an introducer 12 and a dilator 14 slidably received within the introducer 12. The introducer 12 has a proximal portion 12a and a distal portion 12b configured for atraumatic insertion through a tissue opening (e.g., a natural or artificial opening in an abdominal wall and/or an intestine).

Figures 2, 3:
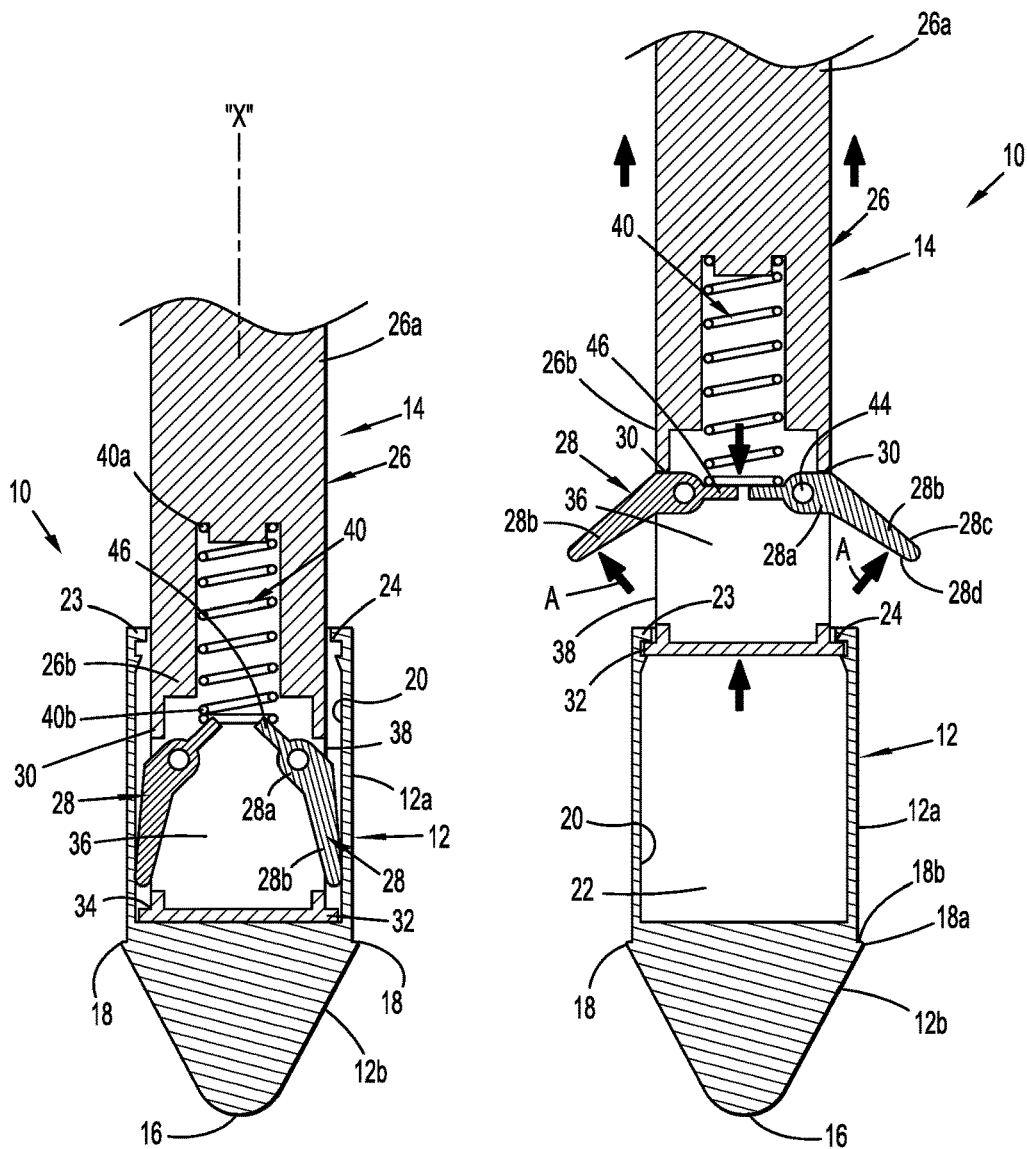
FIG. 2 is a cross-sectional view taken along lines 2-2 of FIG. 1 of the surgical apparatus illustrating the dilator in a retracted state.
FIG. 3 is the cross-sectional view of FIG. 2 illustrating the dilator of the surgical apparatus in an expanded state.

With reference to FIGS. 1-3, the distal portion 12b of the introducer 12 is cone-shaped and terminates in a blunt distal tip 16. In some embodiments, the distal portion 12b of the introducer 12 may assume any suitable shape designed for atraumatic insertion through a tissue opening. The distal portion 12b of the introducer 12 may fabricated from a pliable material, such as, for example, an elastomer and may be solid or alternatively hollow. The distal portion 12b includes a lip or anchor 18 that extends radially outward from the introducer 12. The lip 18, which may be annular, is configured to resist and/or prevent proximal movement of the introducer 12 while the introducer 12 is disposed in tissue (e.g., an intestine), but to allow for the introducer 12 to move distally within the tissue. In embodiments, the lip 18 defines a distal surface 18a that tapers outwardly in a proximal direction and a proximal surface 18b that is substantially orthogonal to a longitudinal axis "X" of the surgical apparatus 10.

The proximal portion 12a of the introducer 12 is cylindrically-shaped and may be monolithically formed with the distal portion 12b. In some embodiments, the proximal portion 12a of the introducer 12 may assume any suitable shape and may be formed separately from and connected to the distal portion 12b. The proximal portion 12a of the introducer 12 has an inner wall 20 that defines a cavity 22 having a cylindrical shape, or alternatively any suitable shape such as rectangular, triangular, or the like. The cavity 22 is dimensioned to slidably receive the dilator 14. The proximal portion 12a of the introducer 12 has an inwardly-extending flange 23 formed by the inner wall 20 which extends into the cavity 22. The flange 23 defines a mating surface 24 configured to complimentarily engage with a mating surface 34 of the dilator 14 to prevent proximal movement of the dilator 14 beyond a proximal end of the introducer 12 as the dilator 14 transitions to an expanded state, as shown in FIG. 3.

With reference to FIGS. 2 and 3, the dilator 14 of the surgical apparatus 10 generally includes an elongate body 26 that is positioned along the longitudinal axis "X" of the surgical apparatus 10 and a plurality of extensions or hooks 28 pivotably coupled to the elongate body 26. The elongate body 26 of the dilator 14 is cylindrically-shaped and is slidably received within the cavity 22 defined in the introducer 12 such that the elongate body 26 is axially movable relative to and within the introducer 12 between a first axial position (FIG. 2) and a second axial position (FIG. 3). In some embodiments, the elongate body 26 of the dilator 14 may assume any suitable shape configured for slidable receipt in the cavity 22 defined in the introducer 12. The elongate body 26 of the dilator 24 includes a proximal portion 26a, which is to be manipulated by a clinician during use of the surgical apparatus 10, and a distal portion 26b disposed within the cavity 22 defined in the introducer 12.

The distal portion 26b of the elongate body 26 includes a plurality of distally-extending stops 30 that are disposed adjacent respective extensions 28 of the plurality of extensions 28. The distal portion 26b of the elongate body 26 further includes a radially-outward extending flange 32 formed at its distal end. The flange 32 defines the mating surface 34 that is configured to abut the mating surface 24 of the introducer 12 when the dilator 14 is in the second axial position, shown in FIG. 3, to prevent the distal end of the dilator 14 from moving proximally beyond the proximal end of the introducer 12.

The distal portion 26b of the elongate body 26 of the dilator 14 defines an inner chamber 36 and a series of side openings 38 in communication with the inner chamber 36. The distal portion 26b includes a biasing member 40, such as, for example, a coil spring, disposed within the inner chamber 36 and oriented along the longitudinal axis "X" of the elongate body 26. In some embodiments, the biasing member 40 may be any suitable spring, such as, for example, a flat spring, a machined spring, a serpentine spring, a cantilever spring, a leaf spring, or the like. The biasing member 40 has a proximal end 40a fixed to the elongate body 26 and a distal end 40b in contact with each of the plurality of extensions 28 to resiliently bias the extensions 28 toward the expanded state.

The extensions 28 of the dilator 14 are configured to maintain the patency of a tissue opening such as an opening in an intestine during formation of a stoma in an ostomy procedure. The extensions 28 are circumferentially disposed about the distal portion 26b of the elongate body 26. The dilator 14 includes at least one extension 28, but in some embodiments may include two or more extensions 28, e.g., four extensions 28.

Each extension 28 of the dilator 14 has a proximal end portion 28a pivotably coupled to the distal portion 26b of the elongate body 26 and a distal end portion 28b. Each of the extensions 28 is pivotable from a retracted or non-deployed state (FIG. 2) in which the extensions 28 are positioned substantially within the cavity 36, to an expanded or deployed state (FIG. 3) in which the extensions 28 project laterally outward from the cavity 36 through the side openings 38 of the dilator 14. The proximal end portion 28a of each of the extensions 28 is pivotably coupled to the elongate body 26 via a pivot pin 44 or alternatively via a swivel connector, a ball and socket connection, or the like. The proximal end portion 28a of each of the extensions 28 is disposed adjacent the respective stops 30 of the elongate body 26. The stops 30 of the elongate body 26 are configured to contact the proximal end portion 28a of each of the respective extensions 28 upon the extensions 28 pivoting to their expanded state to limit the outward movement of the extensions 28.

The proximal end portion 28a of each of the extensions 28 defines a beam 46 disposed on an opposite side of the pivot pin 44 of the extension 28 as the distal end portion 28b. The beam 46 of each of the extensions 28 is in contact with the distal end 40b of the biasing member 40 such that the biasing member 40 imparts a distally-oriented bias on the beam 46 of each of the extensions 28. As such, the distal end portion 28b of each of the extensions 28 is urged to rotate upwardly as indicated by arrows "A" in FIG. 3 about the pivot pin 44 to move the extensions 28 through the side openings 38.

The distal end portion 28b of each of the extensions 28 moves through the respective side openings 38 in the elongate body 26 as the extensions 28 pivot between their retracted and expanded states. In the expanded state, the distal end portion 28b of each of the extensions 28 projects through the respective side openings 38 in the elongate body 26 and laterally outward from the distal portion 26b of the elongate body 26.

In the expanded state, the proximal end portion 28a of each of the extensions 28 is substantially perpendicular to the longitudinal axis "X" of the elongate body 26, and the distal end portion 28b of each of the extensions 28 is angled in a distal direction relative to the longitudinal axis "X" from between about 0 degrees and about 90 degrees. In some embodiments, the distal end portion 28b may extend at about a 45 degree angle relative to the longitudinal axis "X" upon the dilator 14 transitioning to its expanded state. In the retracted state, the distal end portion 28b of each of the extensions 28 is substantially parallel with the longitudinal axis "X" of the elongate body 26.

The distal end portion 28b of each of the extensions 28 has a top surface 28c and a bottom surface 28d. The top surface 28c contacts the inner wall 20 of the introducer 12 when the dilator 14 is in the first axial position (FIG. 2), wherein the dilator 14 is prevented from being moved by the biasing member 40 from the retracted state towards the expanded state. The bottom surface 28d is configured to contact tissue when the dilator 14 is moved to the second axial position (FIG. 3) to maintain the patency of a tissue opening during a surgical procedure such as an ostomy, as will be described in detail below. In some embodiments, distal tips of the extensions 28 are configured to contact tissue instead of or in addition to the bottom surface 28d.

With reference to FIGS. 4-7, an ostomy procedure implementing the surgical apparatus 10 of the present disclosure will be described. An abdominal region "AR" of a patient's body includes abdominal tissue having an outer cutaneous layer "c" (e.g., epidermis, dermis, and hypodermis) and an inner muscle or tissue layer "m" (e.g., anterior rectus sheath) that enshroud organs, vessels, and/or other tissue for performing various bodily functions such as digestion. The stomach and the intestines of a patient's body are supported in the abdominal region "AR" and form part of a patient's digestive system. In the course of a natural digestion process, the stomach and the intestines collaborate with the rest of the digestive system to process food and excrete fecal matter through the anus. Unfortunately, as a result of disease or injury to the intestines, it may become necessary to bypass natural digestion by providing an artificial stoma through the abdominal region in order to safely excrete the fecal matter from the subject's body. To create the stoma, the end margins "e" of the intestine or colon "i" are advanced through an opening "o" in the abdominal wall formed via a scalpel or the like and at least partially flared outwardly to define the opening "o." In an ostomy procedure, the end margins "e" are secured to the cutaneous layer "c" and the underlying muscle layer "m" to create the stoma and effect the colostomy, ileostomy, or the like.

Figure 4:
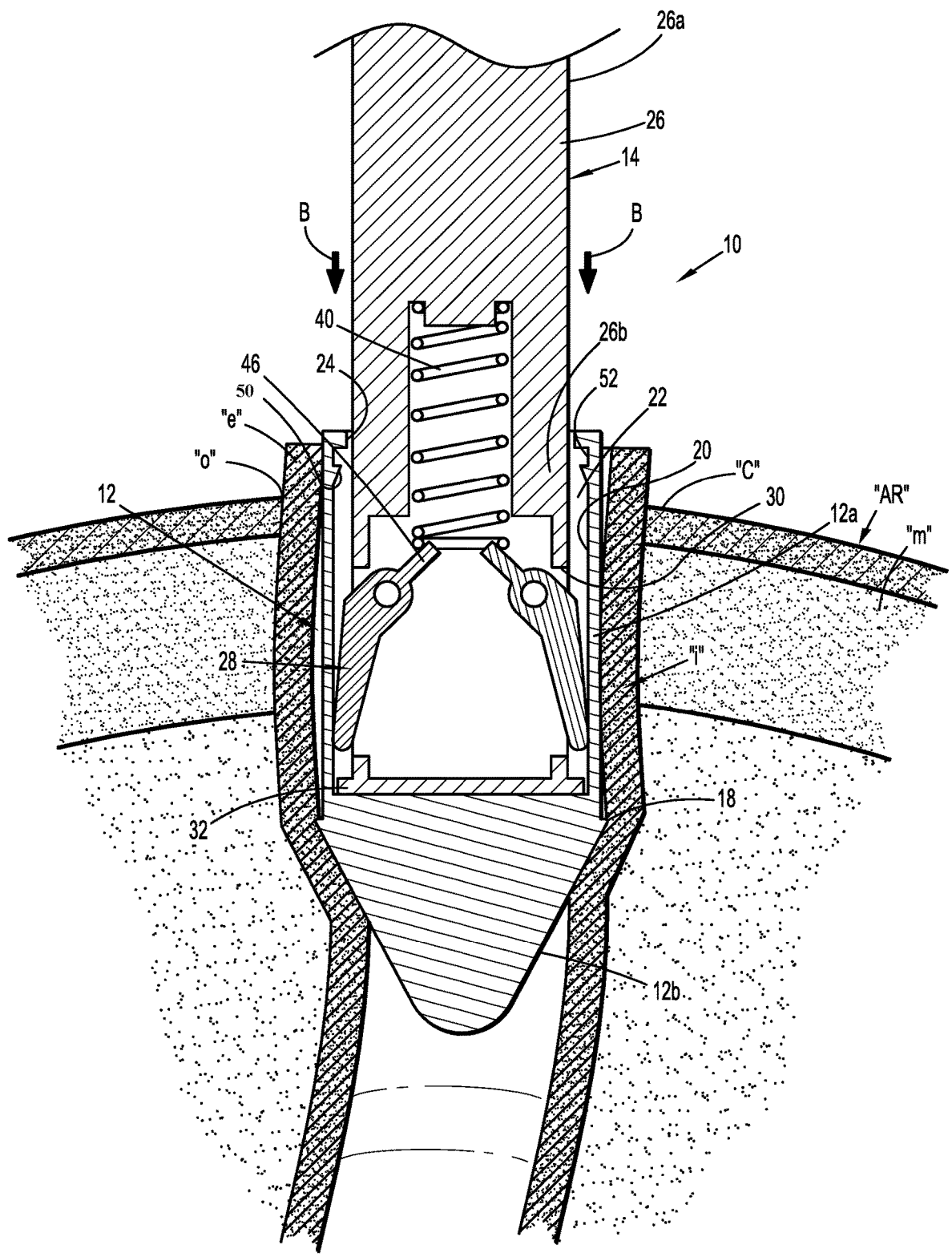
FIG. 4 is the cross-sectional view of FIG. 2 with the surgical apparatus inserted in an opening in an abdominal wall and through an intestine.
Figure 5:
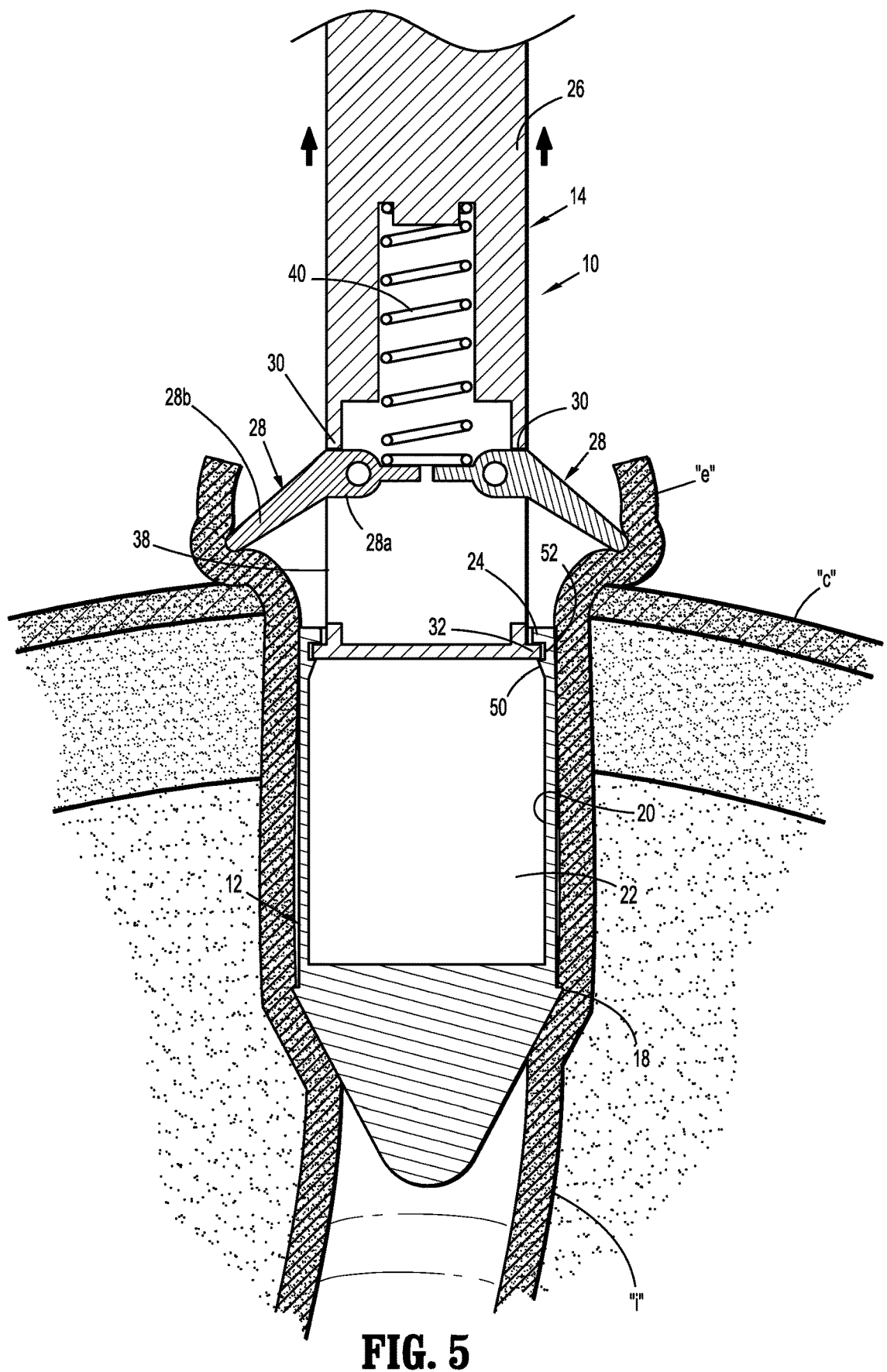
FIG. 5 is the cross-sectional view of FIG. 4 illustrating the dilator in an expanded state engaging end margins of the intestine.

Referring to FIG. 4, prior to securing the end margins "e" to the cutaneous layer "c" and the underlying muscle layer "m," the surgical apparatus 10 of the present disclosure may be inserted into the opening "o" in the abdominal wall and into the intestine "i" to maintain the patency of the opening in the intestine "i" and to outwardly flare the end margins "e" of the intestine "i" into engagement with the cutaneous layer "c." In particular, the introducer 12 of the surgical apparatus 10, with the dilator 14 in the first axial position (i.e., a distal-most position) within the introducer 12, is initially inserted into the intestine "i" and slid distally until the introducer 12 is entirely disposed within the intestine "i." With the introducer 12 inserted a selected distance within the intestine "i," the proximal portion 26a of the elongate body 26 of the dilator 14 is moved proximally relative to the introducer 12 from the first axial position, as shown in FIG. 4, toward the second axial position, as shown in FIG. 5. The introducer 12 remains stationary relative to the intestine "i" as the dilator 14 is moved proximally due to the lip 18 of the introducer 12 anchoring into the intestinal tissue. In embodiments, the introducer 12 may be moved proximally with the lip 18 anchored to the intestinal tissue to withdraw the intestinal tissue through the opening "o."

Referring also to FIG. 5, while the dilator 14 is in the first axial position (FIG. 4), the extensions 28 of the dilator 14 are prevented from pivoting outwardly by the inner wall 20 of the introducer 12. As the dilator 14 moves proximally to the second axial position (FIG. 5), the extensions 28 exit the cavity 22 of the introducer 12 and disengage the inner wall 20 of the introducer 12. Without the inner wall 20 of the introducer 12 constraining the extensions 28 within the cavity 22 of the introducer 12, the extensions 28 are free to pivot outwardly relative to the elongate body 26 via the distally-oriented force of the biasing member 40 exerted on the beam 46 of each of the extensions 28. As the extensions 28 pivot laterally outward through the side openings 38 of the elongate body 26, the distal end portions 28b of the extensions 28 engage the end margins "e" of the intestine "i" to flare the end margins "e" outwardly. Since the extensions 28 are disposed circumferentially about the elongate body 26 of the dilator 14, the entire circumference of the end margins "e" of the intestine "i" is flared outwardly by the extensions 28.

As the elongate body 26 of the dilator 14 moves relative to the introducer 12 toward the second axial position, the flange 32 of the dilator 14 moves over a ramped portion 50 of the inner wall 20 of the introducer 12 providing tactile feedback to the clinician indicating that the dilator 14 is almost in the fully expanded state. The dilator 14 is slid proximally over the ramped portion 50 of the introducer 12 and the flange 32 of the dilator 14 is received within an aperture 52 defined in the inner wall 20 of the introducer 12, locking the dilator 14 in the second axial position. The mating surface 24 of the introducer 12 and the mating surface 34 of the flange 32 of the dilator 14 abut one another so that further proximal movement of the dilator 14 relative to the introducer 12 is inhibited.

When the elongate body 26 of the dilator 12 is in the second axial position, the proximal end portion 28a of each of the extensions 28 contacts the respective stops 30 of the elongate body 26, to inhibit further outward pivoting of the extensions 28. In the fully expanded state, the distal end portion 28b of each of the extensions 28 is oriented downwardly (i.e., distally) at an angle to urge the end margins "e" of the intestine "i" in a downward (i.e., distal) direction. To make the end margins "e" of the intestine "i" flush or substantially flush with the cutaneous layer "c," the dilator 12 may be moved distally relative to the opening "o," thereby pushing the end margins "e" of the intestine "i" further into engagement with the cutaneous layer "c."

Figure 6:
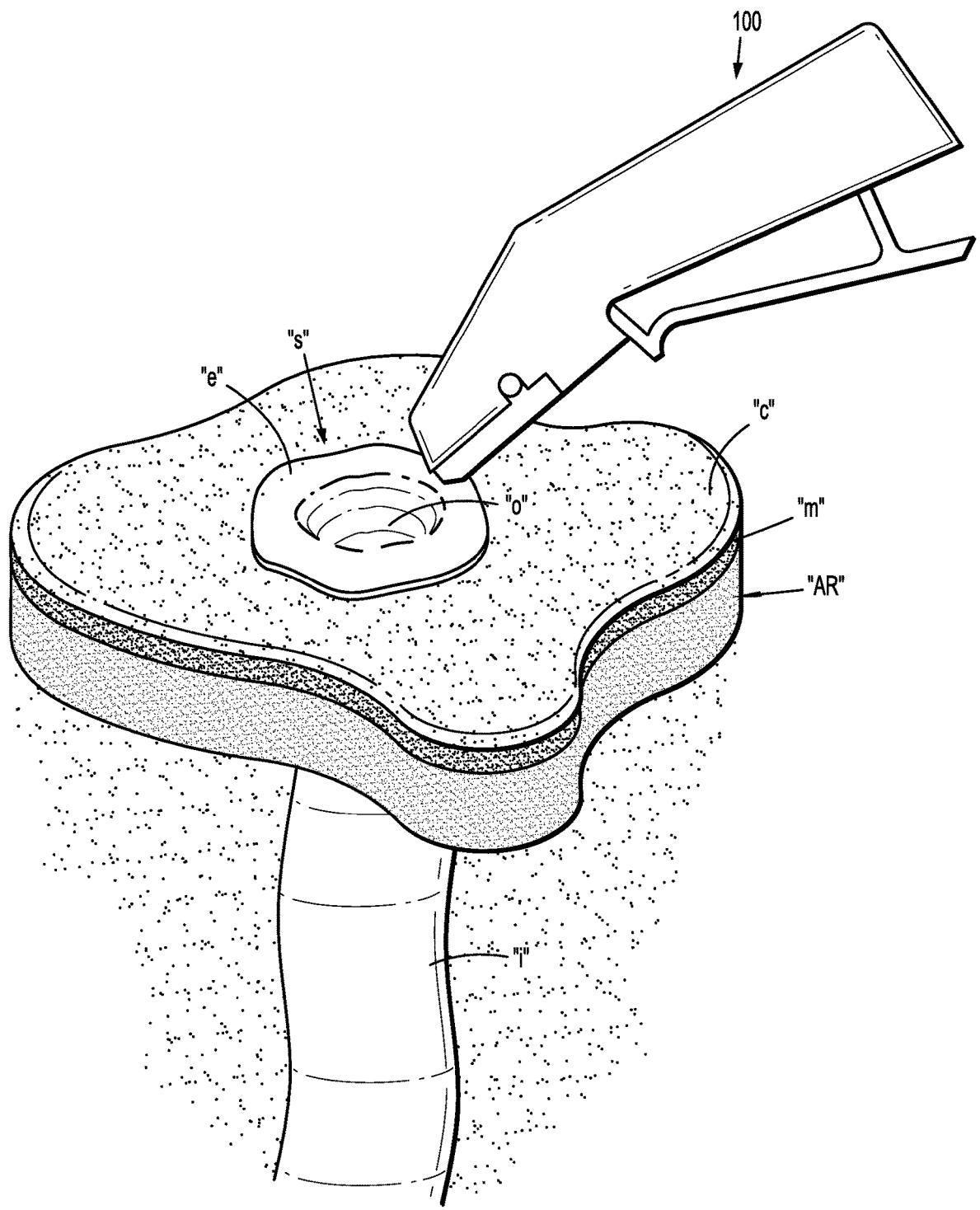
FIG. 6 is a perspective view of an abdominal region illustrating a stapler used to staple the end margins of the intestine to the abdominal wall to form the stoma.
Figure 7:
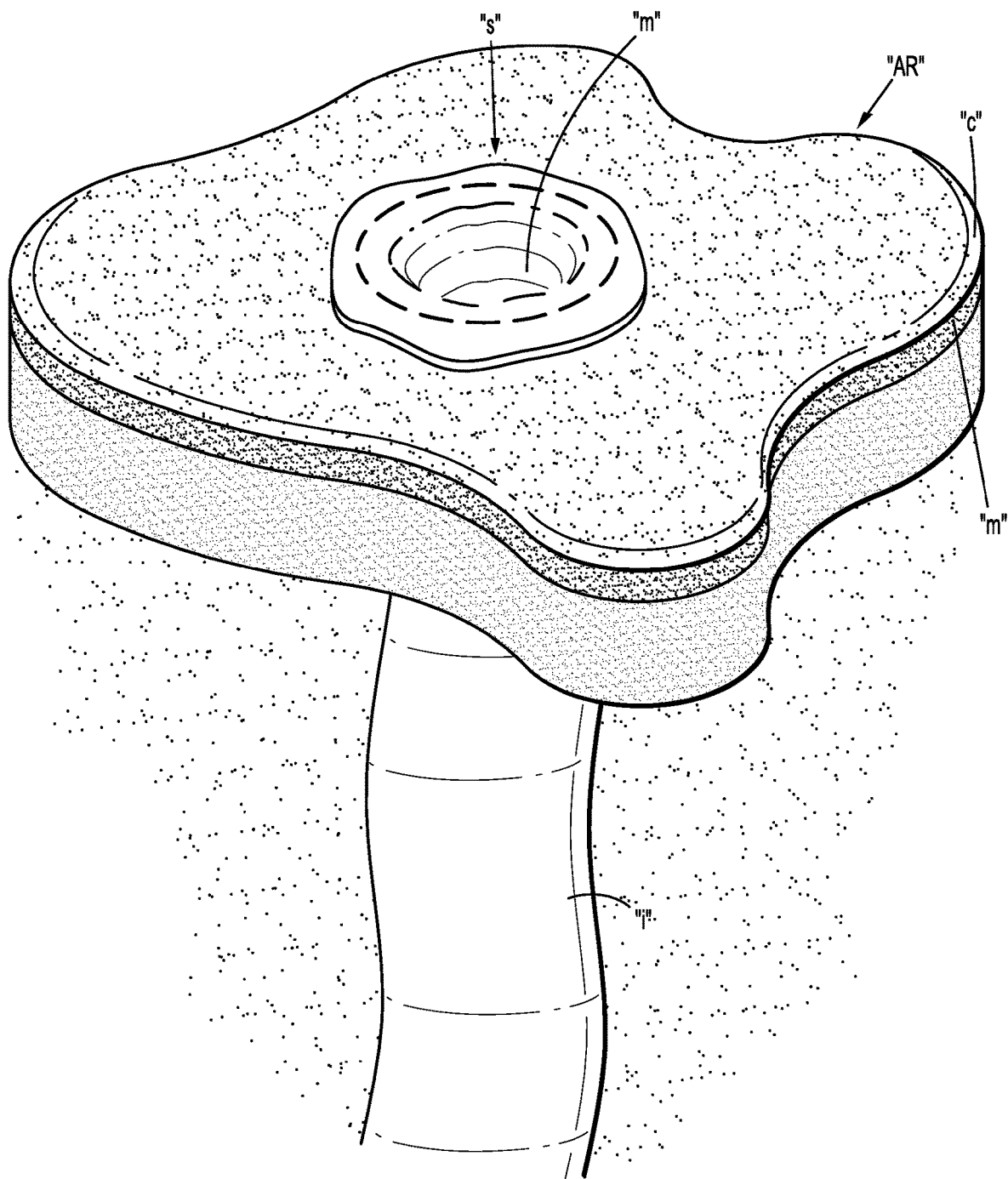
FIG. 7 is a perspective view of the abdominal region shown in FIG. 6 illustrating the stoma formed and stapled to a cutaneous layer of the abdominal region.
Figure 8:
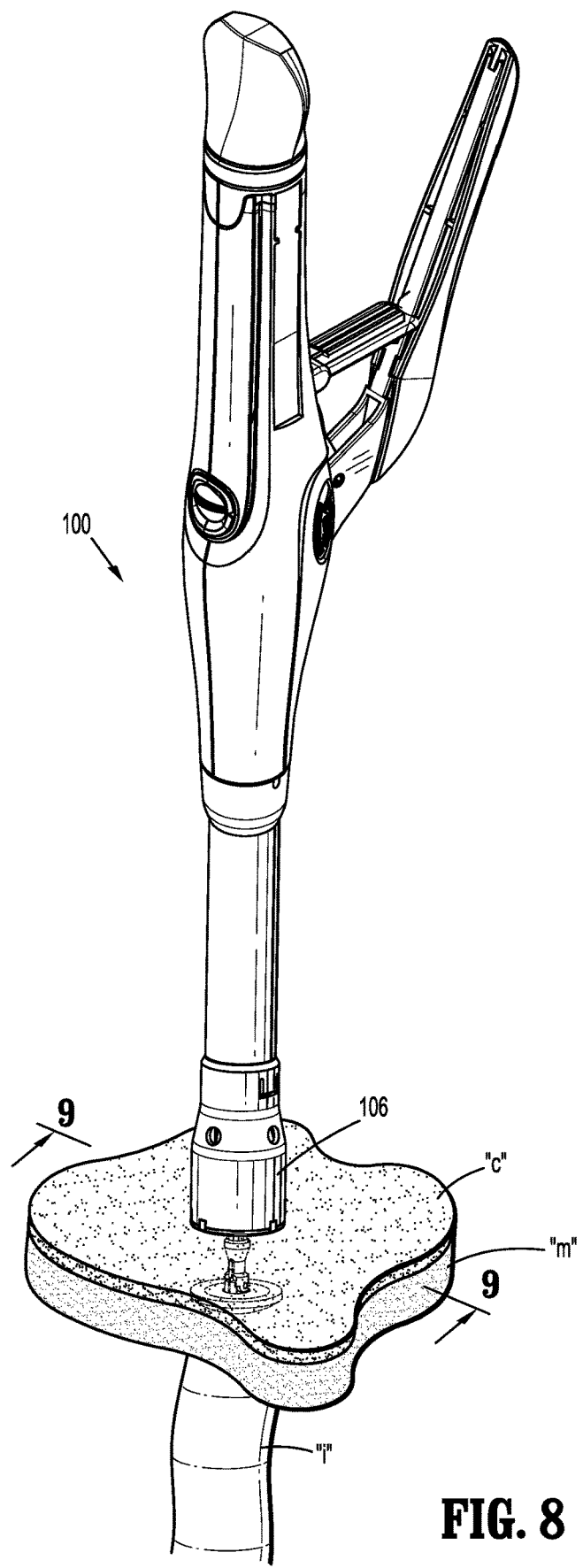
FIG. 8 is a perspective view of a stapling instrument extending into the intestine prior to stapling end margins of the intestine to the abdominal wall to form a stoma.
Figure 9:
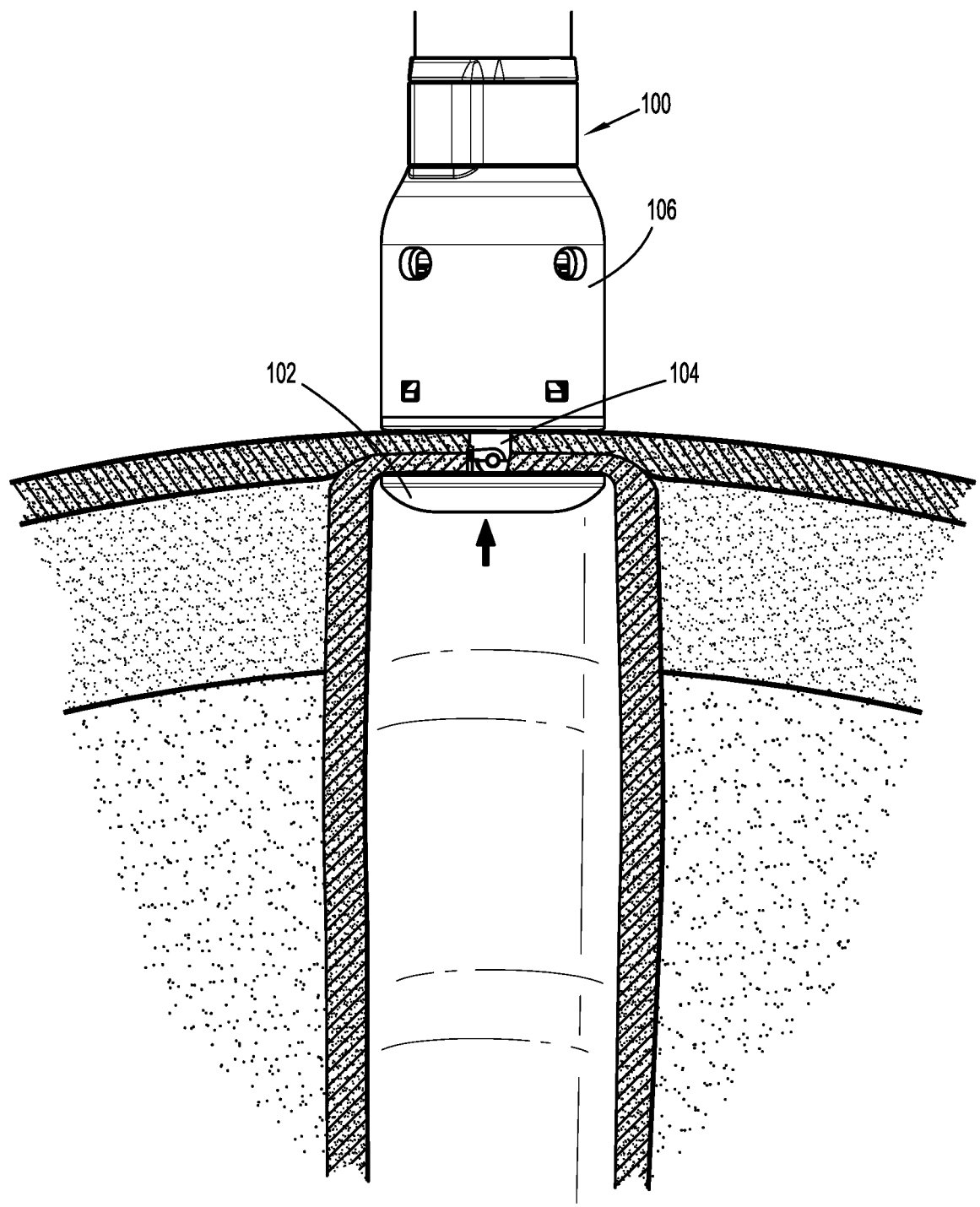
FIG. 9 is a cross-sectional view taken along lines 9-9 of FIG. 8 illustrating the stapling instrument clamping the end margins of the intestine between an anvil and a stapling head of the stapling instrument.
Figure 10:
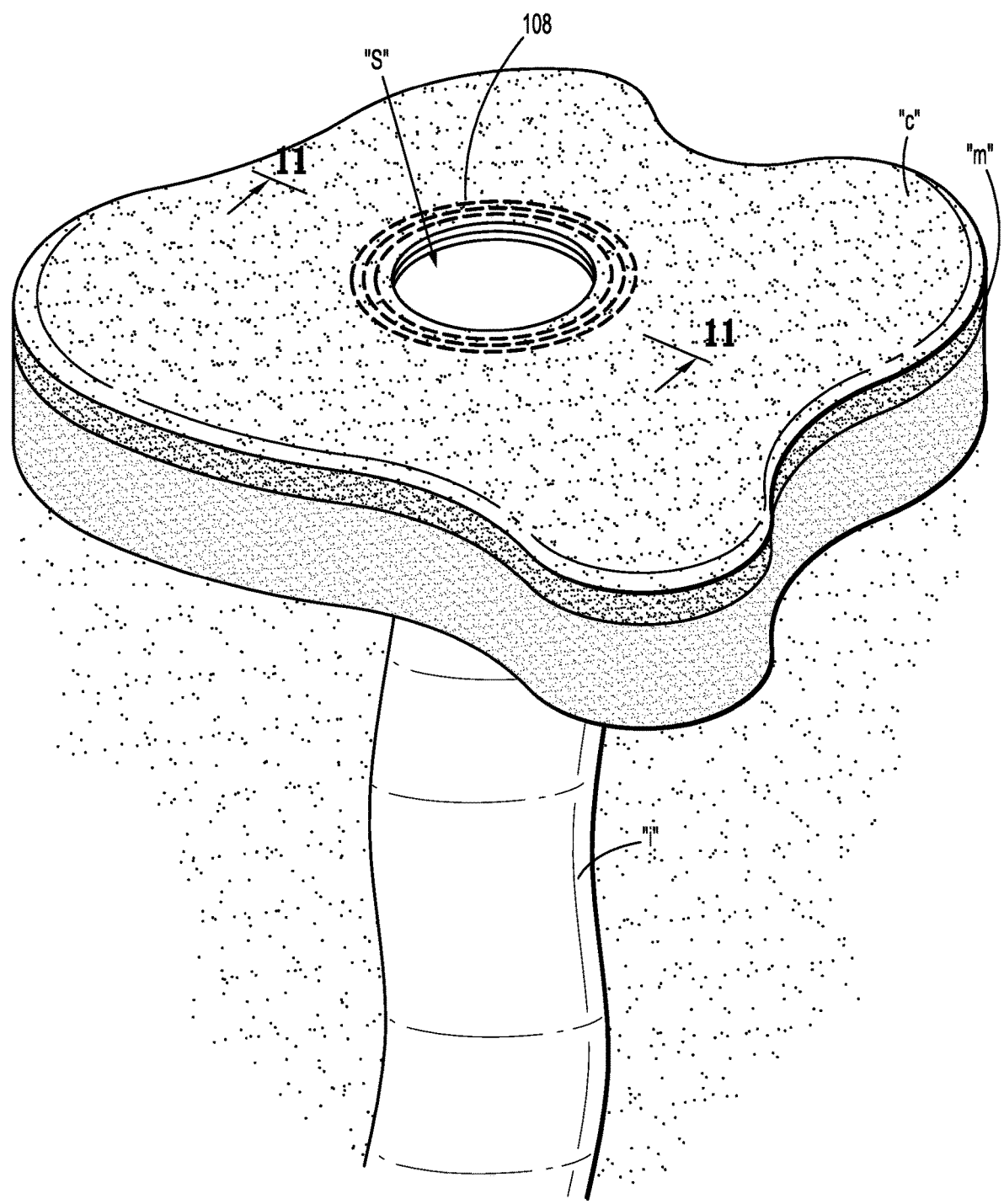
FIG. 10 is a perspective view of an abdominal region illustrating a stoma formed using the stapling instrument of FIG. 8.
Figure 11:
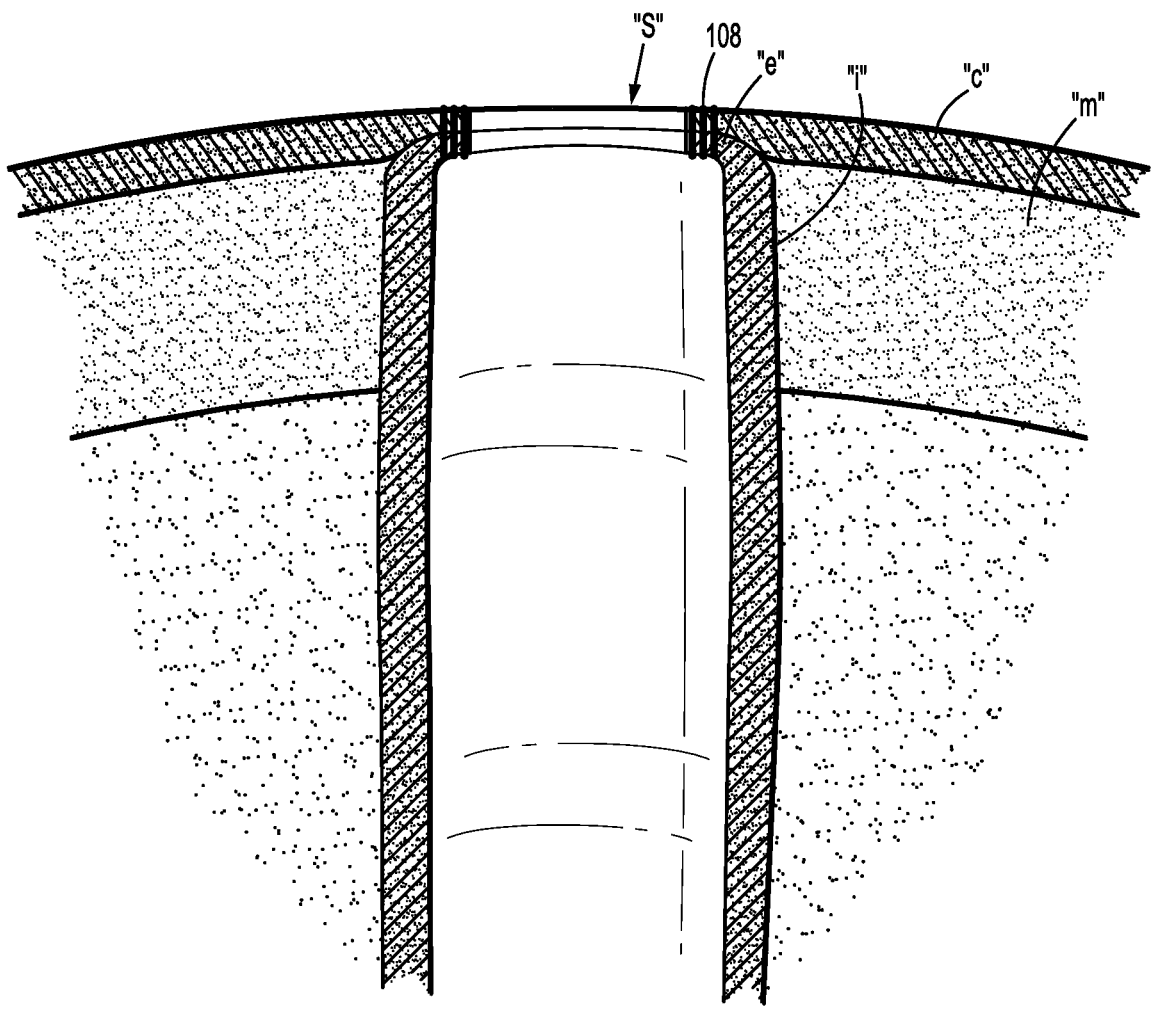
FIG. 11 is a cross-sectional view taken along lines 11-11 of FIG. 10 illustrating staples fastening the end margins of the intestine to an abdominal wall.

Referring to FIG. 6, with the end margins "e" of the intestine "i" held flush against the cutaneous layer "c" by the extensions 28 of the dilator 12, a stapler, such as, for example, a skin stapler 100, may be used to fix the end margins "e" of the intestine "i" to the cutaneous layer "c" and the underlying muscle layer "m" to create the stoma "s" and complete the ostomy. The skin stapler 100 used may be similar to that disclosed in commonly assigned U.S. Pat. No. 5,443,197 to Malis, the entire contents of which are incorporated by reference herein. In some embodiments, rather than using a stapler to create the stoma "s," sutures or any other suitable fastener (e.g., an adhesive) may be applied to the end margins "e." After the stoma "s" is secured to the abdominal region "AR" (FIG. 7), a force oriented in a proximal direction is applied to the surgical apparatus 10 to dislodge the lip 18 of the introducer 12 from engagement with the intestinal tissue and the surgical apparatus 10 is withdrawn from the opening "o."

FIGS. 8-11 illustrate another embodiment of a methodology for facilitating formation of a stoma in connection with an ostomy procedure. In this embodiment, a circular, or an end-to-end anastomosis stapling instrument 100 is implemented to secure the end margins "e" of the intestine "i" to the muscle tissue "m" and, optionally, the cutaneous tissue "c." The circular stapling instrument 100 used may be, e.g., the instrument disclosed in commonly assigned U.S. Patent Publication No. 2015/0115015 to Prescott et al., the entire contents of which are incorporated by reference herein.

In this method, rather than pulling the end margins "e" of the intestine "i" out through the opening "o" in the abdominal wall, the end margins "e" remain under the cutaneous tissue "c." In addition, the end margins "e" are flared inwardly to abut the inner surface of the cutaneous layer "c" rather than flaring the end margins "e" outwardly to abut the outer surface of the cutaneous tissue "c."

An anvil 102 of the circular stapler 100 is positioned beneath the inner layer of the cutaneous tissue "c" and in abutment with the end margins "e" of the intestine "i." An anvil shaft 104 projects upwardly from the anvil 102 and is configured for detachable engagement with a stapler head 106 of the circular stapler 100. Purse string (not explicitly shown) is used to temporarily secure the anvil 102 in the selected position within the abdominal tissue so that the anvil shaft 104 protrudes from the opening in the abdominal tissue and is coaxial with a central axis defined by the intestine "i."

The anvil 102 may include a plurality of recesses or pockets which engage staple legs of a staple or clip to bend the staple legs into a general "B"-shape within the abdominal tissue. The circular stapler 100 is positioned in registration with the end margins "e," and the anvil shaft 104 is attached to the head 106 of the stapling instrument 100. The circular stapler 100 may be actuated to deliver an annular array of staples through the cutaneous tissue "c" and then the end margins "e," whereby the staple legs of the staples 108 are crimped or bent within the pockets of the anvil 102. The circular stapler 100 then actuates a circular blade (not explicitly shown) to cut out the flared end margins "e" and an annular portion of the cutaneous tissue "c" located directly above the flared end margins "e," thereby forming a stoma "s." Subsequent to creation of the stoma "s," the anvil 102 may be removed.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A surgical apparatus configured to be used in an ostomy procedure, comprising:
    an introducer having a tapered distal end portion configured for atraumatic distal insertion into a tissue opening; and
    a dilator including:
        an elongate body having a distal portion disposed within the introducer and being axially movable in a proximal direction relative to the introducer from a first position to a second position;
        at least one extension movably coupled to the elongate body, wherein the at least one extension is movable from a retracted state to an expanded state in response to proximal movement of the elongate body of the dilator relative to the introducer from the first position to the second position, wherein when the at least one extension is in the retracted state the at least one extension is disposed within the introducer, and when the at least one extension is in the expanded state the at least one extension projects laterally outward from the distal portion of the elongate body; and
        a biasing member disposed within the elongate body, wherein the biasing member biases the at least one extension toward the expanded state.

2. The surgical apparatus according to claim 1, wherein the dilator is configured to move axially relative to the introducer between the first position and the second position, in which the at least one extension of the dilator is disposed outside of the introducer.

3. The surgical apparatus according to claim 2, wherein the dilator slides proximally relative to the introducer from the first position to the second position.

4. The surgical apparatus according to claim 2, wherein the introducer is configured to prevent the dilator from moving proximally relative to the introducer when the dilator is in the second position.

5. The surgical apparatus according to claim 4, wherein the dilator has a mating surface disposed at the distal portion of the elongate body and the introducer has a mating surface disposed at a proximal portion thereof such that the mating surface of the dilator contacts the mating surface of the introducer in the second position.

6. The surgical apparatus according to claim 1, wherein the at least one extension has a proximal end portion pivotably coupled to the elongate body and disposed within the elongate body, the biasing member in engagement with the proximal end portion.

7. The surgical apparatus according to claim 1, wherein the at least one extension has a proximal end portion pivotably coupled to the elongate body and a distal end portion, the distal end portion rotating in a proximal direction during movement of the at least one extension from the retracted state to the expanded state.

8. The surgical apparatus according to claim 7, wherein the distal portion of the elongate body has a stop configured to engage the proximal end portion when the at least one extension is moved to the expanded state.

9. The surgical apparatus according to claim 7, wherein the distal end portion is disposed in oblique relation to the proximal end portion.

10. The surgical apparatus according to claim 7, wherein in the expanded state, the proximal end portion is substantially perpendicular with a longitudinal axis defined by the elongate body and the distal end portion is angled in a distal direction relative to the longitudinal axis.

11. The surgical apparatus according to claim 7, wherein the distal end portion is in engagement with an inner wall of the introducer when the at least one extension is in the retracted state.

12. The surgical apparatus according to claim 11, wherein the dilator is movable in a proximal direction relative to the introducer between the first position, in which the distal end portion is in engagement with the inner wall of the introducer, and the second position, in which the distal end portion is out of engagement with the inner wall of the introducer.

13. The surgical apparatus according to claim 1, wherein the at least one extension includes a plurality of extensions disposed circumferentially about the distal portion of the elongate body.

14. A surgical apparatus configured to be used in an ostomy procedure, comprising:
    an introducer configured for atraumatic insertion into a tissue opening; and
    a dilator including:
        an elongate body having a distal portion disposed within the introducer and being axially movable relative to the introducer from a first position to a second position; and
        at least one extension movably coupled to the elongate body, the at least one extension being movable from a retracted state to an expanded state in response to movement of the elongate body of the dilator relative to the introducer from the first position to the second position, the at least one extension disposed within the introducer in the retracted state, and the at least one extension projecting laterally outward from the distal portion of the elongate body in the expanded state, the elongate body of the dilator being configured to move axially relative to the introducer between the first position and the second position, in which the at least one extension of the dilator is disposed outside of the introducer, the introducer being configured to prevent the dilator from moving proximally relative to the introducer when the elongate body of the dilator is in the second position, wherein the dilator has a mating surface disposed at the distal portion of the elongate body and the introducer has a mating surface disposed at a proximal portion of the dilator such that the mating surface of the dilator contacts the mating surface of the introducer in the second position.

15. The surgical apparatus according to claim 14, wherein the dilator includes a biasing member disposed within the elongate body, the biasing member biasing the at least one extension toward the expanded state.

16. The surgical apparatus according to claim 15, wherein the at least one extension has a proximal end portion pivotably coupled to the elongate body and disposed within the elongate body, the biasing member in engagement with the proximal end portion.

17. A surgical apparatus configured to be used in an ostomy procedure, comprising:
   an introducer configured for atraumatic insertion into a tissue opening; and
   a dilator including:
      an elongate body having a distal portion disposed within the introducer and being axially movable relative to the introducer from a first position to a second position; and
      at least one extension movably coupled to the elongate body, the at least one extension being movable from a retracted state to an expanded state in response to movement of the elongate body of the dilator relative to the introducer from the first position to the second position, the at least one extension disposed within the introducer in the retracted state, and the at least one extension projects laterally outward from the distal portion of the elongate body in the expanded state, the at least one extension having a proximal end portion pivotably coupled to the elongate body and a distal end portion, the distal end portion rotating in a proximal direction during movement of the at least one extension from the retracted state to the expanded state, wherein the distal end portion is in engagement with an inner wall of the introducer when the at least one extension is in the retracted state.

18. The surgical apparatus according to claim 17, wherein the elongate body of the dilator is movable in a proximal direction relative to the introducer between the first position, in which the distal end portion is in engagement with the inner wall of the introducer, and the second position, in which the distal end portion is out of engagement with the inner wall of the introducer.

19. The surgical apparatus according to claim 1, wherein the distal portion of the elongate body defines at least one side opening through which the at least one extension extends when the at least one extension is in the expanded state.

\* \* \* \* \*